United States Patent [19]
Asato et al.

[11] Patent Number: 4,916,154
[45] Date of Patent: Apr. 10, 1990

[54] 23-IMINO DERIVATIVES OF LL-F28249 COMPOUNDS

[75] Inventors: Goro Asato, Titusville; Donald J. France, Pennington, both of N.J.

[73] Assignee: American Cyanamid Company, Stamford, Conn.

[21] Appl. No.: 88,953

[22] Filed: Aug. 27, 1987

Related U.S. Application Data

[63] Continuation-in-part of Ser. No. 907,283, Sep. 12, 1986, abandoned.

[51] Int. Cl.$^4$ .................. A61K 31/335; C07D 313/06
[52] U.S. Cl. ...................................... 514/450; 549/264
[58] Field of Search ........................ 549/264; 514/450

[56] References Cited

U.S. PATENT DOCUMENTS

| 4,289,760 | 9/1981 | Mrozik et al. | 536/7.1 |
| 4,423,209 | 12/1983 | Mrozik | 536/7.1 |
| 4,427,663 | 1/1984 | Mrozik | 514/30 |
| 4,457,920 | 7/1984 | Mrozik | 549/264 |
| 4,547,520 | 10/1985 | Ide et al. | 549/264 |
| 4,579,864 | 4/1986 | Linn et al. | 549/264 |
| 4,806,527 | 2/1989 | Christensen et al. | 514/30 |

FOREIGN PATENT DOCUMENTS

| 170006 | 2/1986 | European Pat. Off. . |
| 2166436A | 5/1986 | United Kingdom . |
| 2176182 | 12/1986 | United Kingdom . |

OTHER PUBLICATIONS

Abstract of Japan Patent No. 142,991 (Jul. 29, 1985).

Primary Examiner—Glennon H. Hollrah
Assistant Examiner—Ba K. Trinh
Attorney, Agent, or Firm—Estelle J. Tsevdos

[57] ABSTRACT

The present invention relates to novel 23-imino derivatives of LL-F28249α, β, γ, δ, ε, ζ, θ, ι, and λ compounds. These LL-F28249 compounds (collectively) are isolates from the fermentation broth of *Streptomyces cyaneogrisesu* subspecies noncyanogenus having deposit accession number NRRL 15773. The precursor 23-oxo compounds are prepared by selectively oxidizing suitably protected 23-hydroxy compounds of LL-F28249 components using oxidizing agents. Subsequently, the 23-oxo compounds are converted to the 23-imino compounds. These novel compounds have potent anthelmintic, insecticidal, ectoparasiticidal, nematicidal and acaricidal activity. Compositions containing these 23-oxo and 23-imino derivatives of LL-F28249 also are described herein.

15 Claims, No Drawings

23-IMINO DERIVATIVES OF LL-F28249 COMPOUNDS

This application is a continuation-in-part of copending application, Ser. No. 06/907,283, filed September 12, 1986, now abandoned.

BACKGROUND OF THE INVENTION

The present invention relates to new 23-oxo (keto) and 23-imino derivatives of the compounds collectively defined as LL-F28249. These LL-F28249 antibiotics preferably are produced by the fermentation of the microorganism *Streptomyces cyaneogriseus* subspecies noncyanogenus, deposited in the NRRL under deposit accession no. 15773. The morphological characteristics, compounds and method for their production is disclosed in U.S. Pat. application Ser. No. 732,252, filed May 10, 1985, which is a continuation-in-part application of Ser. No. 617,650, filed June 5, 1984 and published in European Patent Application Publication No. 170,006, incorporated herein by reference thereto.

The LL-F28249 components α–λ are complex macrolides which have a 23-hydroxy substituent, as well as two other hydroxy groups. The selective oxidation of this 23-hydroxy group to a 23-oxo group and the subsequent derivatization of the oxo group to afford 23-imino derivatives are the subject matter of the present invention. These 23-oxo and 23-imino derivatives of the LL-F28249 α–λ compounds are useful for the prevention, treatment or control of helmintic, ecotparasitic, insect, acarid and nematode infections and infestations in warm-blooded animals and agricultural crops.

SUMMARY OF THE INVENTION

The present invention provides novel 23-oxo (keto) and 23-imino derivatives of the compounds designated LL-F28249 alpha through lambda.

The LL-F28249α–λ compounds have the following structural formula:

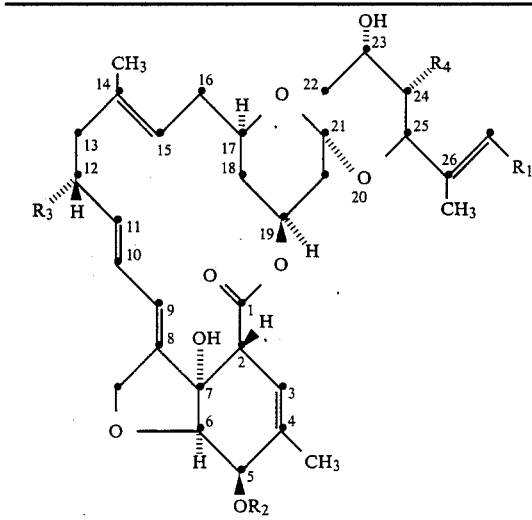

| Component | $R_1$ | $R_2$ | $R_3$ | $R_4$ |
|---|---|---|---|---|
| LL-F28249α | CH(CH$_3$)$_2$ | H | CH$_3$ | CH$_3$ |
| LL-F28249β | CH$_3$ | H | CH$_3$ | CH$_3$ |
| LL-F28249γ | CH$_3$ | CH$_3$ | CH$_3$ | CH$_3$ |
| LL-F28249ε | CH(CH$_3$)$_2$ | H | H | CH$_3$ |
| LL-F28249ζ | CH$_2$CH$_3$ | H | CH$_3$ | CH$_3$ |
| LL-F28249θ | CH(CH$_3$)$_2$ | H | CH$_3$ | CH$_2$CH$_3$ |
| LL-F28249ι | CH(CH$_3$)$_2$ | H | CH$_2$CH$_3$ | CH$_3$ |
| LL-F28249λ | CH(CH$_3$)$_2$ | CH$_3$ | CH$_3$ | CH$_3$ |

The compounds of the present invention are useful anthelmintics, ectoparasiticides, insecticides, acaricides and nematicides in treating, preventing or controlling such diseases in warm-blooded animals, such as poultry, cattle, sheep, swine, rabbits, horses, dogs, cats and human beings and agricultural crops.

Although these diseases have been recognized for years and therapies exist for the treatment and prevention of the diseases, the present invention provides novel compounds in the search for effective such therapy. For instance, U.S. patent application Ser. Nos. 907,186, 907,187, 907,188, 907,259, 907,281 and 907,284 of Asato and Asato et al, filed September 12, 1986 and incorporated herein by reference thereof provide compounds for such treatments.

U.S. Pat. No. 3,950,360, Aoki et al, April 13, 1976 discloses certain antibiotic substances obtained by culturing a Streptomyces microorganism, said compounds being useful as insecticides and acaricides. Further, an entire series of U.S. patents relates to certain compounds produced by the fermentation of *Streptomyces avermitilis* (U.S. Pat. No. 4,171,314, Chabala et al, October 16, 1979; U.S. Pat. No. 4,199,569, Chabala et al, April 22, 1980; U.S. Pat. No. 4,206,205, Mrozik et al, June 3, 1980; U.S. Pat. No. 4,310,519, Albers-Schonberg, January 12, 1982; U.S. Pat. No. 4,333,925, Buhs et al, June 8, 1982). U.S. Pat. No. 4,423,209, Mrozik, December 27, 1983 relates to the process of converting some of these less desirable components to more preferred ones. Finally, British Patent Application No. 2166436 A discloses antibiotics also.

The present compounds or the pharmaceutically and pharmacologically acceptable salts thereof exhibit excellent and effective treatment, prevention and/or control of these serious diseases of warm-blooded animals.

It is an object of the present invention, therefore, to provide novel 23-oxo and 23-imino derivatives of LL-F28249α–λ. It is a further object to provide a process for the preparation of these derivatives and to provide methods for preventing, treating or controlling endo and ectoparasitic (collectively parasitic), insect, nematode, acarid and helmintic diseases and infestation in warm-blooded animals and agricultural crops by providing compositions containing prophylactically, therapeutically or pharmaceutically-effective amounts of the present novel compounds.

These and other objects of the invention will become apparent by the more detailed description of the invention provided hereinbelow.

DETAILED DESCRIPTION OF THE INVENTION

The LL-F28249 compounds which may act as precursors of the present compounds are represented by the following structural formula,

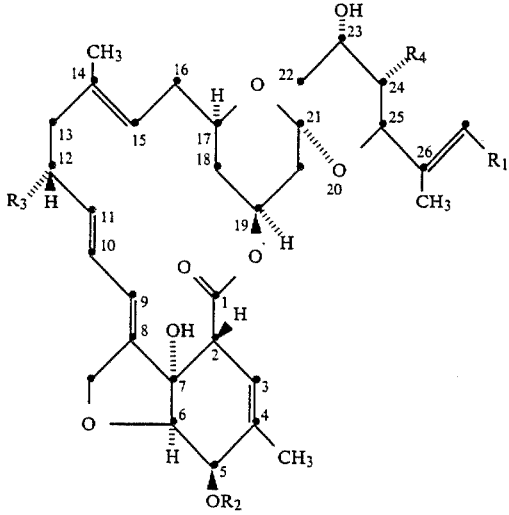

| Component | R₁ | R₂ | R₃ | R₄ |
|---|---|---|---|---|
| LL-F28249α | CH(CH₃)₂ | H | CH₃ | CH₃ |
| LL-F28249β | CH₃ | H | CH₃ | CH₃ |
| LL-F28249γ | CH₃ | CH₃ | CH₃ | CH₃ |
| LL-F28249ε | CH(CH₃)₂ | H | H | CH₃ |
| LL-F28249ζ | CH₂CH₃ | H | CH₃ | CH₃ |
| LL-F28249θ | CH(CH₃)₂ | H | CH₃ | CH₂CH₃ |
| LL-F28249ι | CH(CH₃)₂ | H | CH₂CH₃ | CH₃ |
| LL-F28249λ | CH(CH₃)₂ | CH₃ | CH₃ | CH₃ | wherein, $R_1$, $R_2$, $R_3$ and $R_4$ are defined by the above table.

The compounds of the instant invention are represented by the following structural formula:

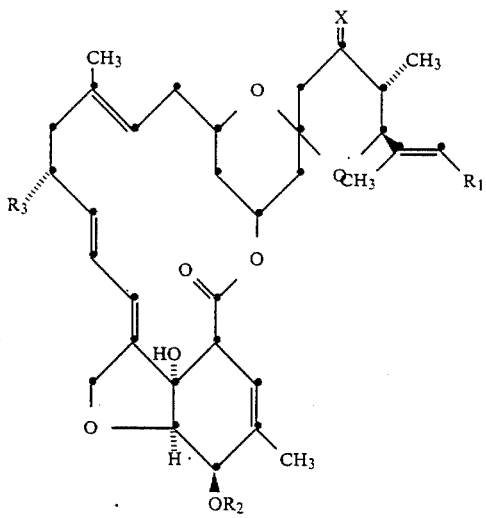

wherein $R_1$ is methyl, ethyl or isopropyl; $R_2$ is hydrogen, methyl, $C_1-C_4$ alkanoyl, methoxyacetyl, chloroacetyl, dichloroacetyl, trichloroacetyl, trifluoroacetyl, phenoxyacetyl, optionally substituted on the phenyl ring with one or two halogens, $C_1-C_4$ alkyl groups, $C_1-C_4$ alkoxy groups or nitro groups, or benzoyl optionally substituted with one or two halogens, $C_1-C_4$ alkyl groups, $C_1-C_4$ alkoxy groups, or nitro groups; $R_3$ is hydrogen or methyl; X is oxygen, NOR₄, or N—NHR₅; R₄ is hydrogen, $C_1-C_6$ alkyl, $C_1-C_4$ alkoxymethyl, benzyl, allyl, propargyl, phenyl, CH₂COO-alkyl ($C_1-C_4$), N-($C_1-C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1-C_6$ alkanoyl, chloroacetyl, methoxyacetyl, phenylacetyl optionally substituted on the phenyl ring with one or two halogens, $C_1-C_4$ alkyl groups, $C_1-C_4$ alkoxy groups or nitro groups, phenoxyacetyl optionally substituted on the phenyl ring by one or two halogens, $C_1-C_4$ alkyl groups, $C_1-C_4$ alkoxy groups or nitro groups, or benzoyl optionally substituted with one or two halogens, $C_1-C_4$ alkyl groups, $C_1-C_4$ alkoxy groups or nitro groups; $R_5$ is

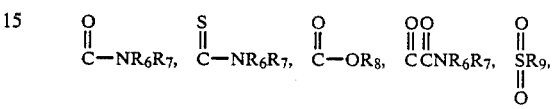

$C_1-C_6$ alkanoyl, formyl, $C_1-C_6$ alkyl,

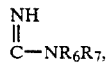

benzoyl optionally substituted with one or two halogens, $C_1-C_4$ alkyl groups, $C_1-C_4$ alkoxy groups or nitro groups; $R_6$ and $R_7$ are hydrogen or $C_1-C_6$ alkyl, or phenyl optionally substituted with one or two halogens, $C_1-C_4$ alkyl, $C_1-C_4$ alkoxy, or phenyl, optionally substituted with one or two halogens, $C_1-C_4$ alkyl groups, $C_1-C_4$ alkoxy groups or nitro groups; $R_8$ is $C_1-C_6$ alkyl or phenyl optionally substituted with one or two halogens, $C_1-C_4$ alkyl groups, $C_1-C_4$ alkoxy groups or nitro groups; $R_9$ is $C_1-C_6$ alkyl or phenyl optionally substituted with one or two halogens, $C_1-C_4$ alkyl groups, $C_1-C_4$ alkoxy groups or nitro groups; and the pharmaceutically and pharmacologically acceptable salts thereof.

Preferably, $R_1$ is isopropyl; $R_2$ is hydrogen or methyl; $R_3$ is methyl; $R_4$ through $R_8$ are as described hereinabove; and X is oxygen, NOR₄, N—NHCH₃ or

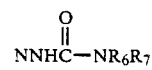

or NNHCOOR₈. A preferred group of compounds of this invention is illustrated by formula I wherein $R_1$ is isopropyl; $R_2$ is hydrogen, $R_3$ is methyl; X is oxygen, NOR₄, or

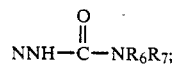

$R_4$ is $C_1-C_3$ alkyl, N-($C_1-C_6$ alkyl)carbamoyl, N-(phenyl)carbamoyl, N-(4-chlorophenyl)carbamoyl, N-(benzyl)carbamoyl, $C_1-C_6$ alkanoyl, chloroacetyl, methoxyacetyl, benzoyl or chlorobenzoyl, and $R_6$ and $R_7$ are as described hereinabove.

A preferred group of compounds of structure (I) are the following: wherein,
$R_1$ is isopropyl;
$R_2$ is hydrogen or methyl;
$R_3$ is methyl;
X is oxygen, NOR₄, N—NHR₅, or

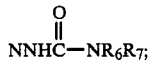

and
R$_4$ through R$_7$ are the above-mentioned groups.

Another preferred group of compounds of structure (I) are the following: wherein,
R$_1$ is isopropyl;
R$_2$ is hydrogen;
R$_3$ is methyl;
X is oxygen, NOR$_4$, N—NHR$_5$, or

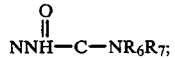

and
R$_4$ through R$_7$ are the above-mentioned group.

The most preferred group of compounds of structure (I) are the following: wherein,
R$_1$ is isopropyl;
R$_2$ is hydrogen;
R$_3$ is methyl;
X is oxygen, NOR$_4$, or

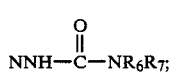

and R$_4$ is
C$_1$–C$_3$ alkyl,
N-(C$_1$–C$_6$ alkyl)carbamoyl,
N-(phenyl)carbamoyl,
N-(4-chlorophenyl)carbamoyl,
N-(benzyl)carbamoyl,
C$_1$–C$_6$-alkanoyl, chloroacetyl, methoxyacetyl, benzoyl and chlorobenzoyl.

In preparing the compounds of the present invention, other hydroxy groups must be protected. Therefore, prior to the oxidation of the 23-hydroxyl group to the 23-oxo or keto group is carried out, the 5-hydroxyl group is protected. Suitable protecting groups are trisubstituted silyl groups, such as t-butyldimethylsilyl and trimethylsilyl, or trisubstituted silyloxyacetyl groups, such as t-butyldimethylsilyloxy acetyl group. The protecting groups, however, are not limited to these groups since other useful protecting groups such as acyl and substituted acyl, such as acetyl, trifluoroacetyl, chloroacetyl, trichloroacetyl, phenoxyacetyl and the like, are also useful in the present process.

One of the preferred protecting groups is t-butyldimethylsilyl. This group is attached to the 5-hydroxyl group by reacting an unprotected 5-hydroxy F-28249 compound with t-butyldimethylsilyl chloride in the presence of a base, such as imidazole, pyridine, 4-dimethylaminopyridine, triethylamine and the like, in an aprotic solvent such as methylene chloride, toluene, ethylacetate, tetrahydrofuran, ethylenedichloride and the like. The reaction is stirred at a temperature of about 0° C. to 30° C., and the reaction is complete in several hours, depending on the temperature of the reaction. The completion of the reaction is usually monitored by high performance liquid chromatography (HPLC) using reverse phase on a Whatman Partisil CCS/C$_8$ rapid analysis column.

Another preferred protecting group is t-butyldimethylsilyloxy acetyl group. This group is attached to the 5-hydroxyl group by combining the unprotected F-28249 compound in an aprotic solvent such as methylene chloride, toluene, ethyl acetate, tetrahyddrofuran, ethylenedichloride and the like, containing a tertiary amine, such as pyridine or triethylamine, and adding the protecting agent in the form of an acide halide. The reaction is conducted at a temperature of about 0° C. to 30° C. and is monitored by HPLC for completion.

The 23-hydroxyl group of the protected F-28249 compound then is oxidized to the 23-oxo (or keto) group by using oxidizing agents such as pyridinium dichromate, pyridiniium chlorochromate, chromic acid-dimethylpyrazole, acetic anhydride/dimethylsulfoxide, trifluoroacetic anhydride/dimethylsulfoxide, N-chlorosuccinimide/dimethylsulfoxide, oxalyl chloride/dimethylsulfoxide and the like. The reaction is carried out at dry-ice bath temperatures (about −78° C.) to room temperature (about 25° C.) and is complete in about 1 to 24 hours, depending on the rate of oxidation, which is monitored by HPLC. The dimethylsulfoxide oxidation procedures are carried out in the presence of triethylamine or diisopropylethylamine. Solvents such as methylene chloride, ethylenedichloride, dimethylformamide, dimethylsulfoxide and the like are used. In using oxalyl chloride/dimethylsulfoxide in the presence of triethylamine, it is advantageous to add molecular sieves to the reaction mixture to increase the yield. The oxidation may also be carried out by soil microorganisms using 100 mg to 10 g of a 23-hydroxy compound per liter of unsterilized soil at 20° C. to 30° C. The oxidized 23-keto compound is extracted from the soil by a solvent such as acetone, methanol or ethanol.

The silyl protecting group is removed by stirring sa protected 23-keto F28249 compound in a lower alkanol such as methanol at 0° to room temperature for about 0.5 hour to an hour in the presence of an acid such a p-toluenesulfonic acid. If the protecting group is a silyloxyacetyl group, the silyl group is removed with acid as described above, and the hydroxyacetyl group is cleaved with an equivalent of base such as sodium methoxide in methanol at 0° to room temperature in 0.5 hour to several hours. The silyloxyacetyl group may also be removed in one step by treatment with sodium methoxide at room temperature until the reaction is complete. Similarly, other acyl protecting groups are removed by base treatment.

The imino derivatives of the 23-oxo compounds are readily prepared by standard techniques such as procedures described by S. M. McElvain in *The Characterization of Organic Compounds*, published by MacMillian Company, New York, 1953, pages 204–205 and incorporated herein by reference.

Typically, a 23-oxo compound is stirred in alcohol, such as methanol or ethanol, or dioxane in the presence of acetic acid and an excess of the amino derivatizing agent, such as hydroxylamine hydrochloride, O-methylhydroxylamine hydrochloride, semicarbazide hydrochloride and the like along with an equivalent amount of sodium acetate, at room temperature to 50° C. The reaction is usually complete in several hours to several days at room temperature but can be readily speeded by heating.

The O-acyloximes or carbamoylated oximes are prepared by treating the oximes of structure (I) with acid anhydrides or isocyanates to afford (I), wherein R$_4$ is C$_1$–C$_6$ alkanoyl, chloroacetyl, methoxyacetyl, phenylacetyl, benzoyl, chlorobenzoyl, N-(C$_1$–C$_4$ alkyl)carbamoyl, N-(allyl)carbamoyl, N-(propargyl)-carbamoyl, N-(phenyl)-carbamoyl, N-(chlorophenyl)carbamoyl, N-(dichlorophenyl)-carbamoyl or N-(benzyl)carbamoyl. The reactions are conducted in inert solvents, such as methylene chloride, ethylenedichloride or dioxane, in the presence of a tertiary amine, such as triethylamine or diisopropylethylamine. Generally, the reactions are conducted from 0° C. to room temperature, but if the reactions are sluggish, heat is applied. An equivalent to a slight excess of the acid anhydride is used to avoid reaction at the 5-hydroxy group.

The novel compounds of the present invention have significant activity as anthelmintics, ectoparasiticides, insecticides, nematicides and acaricides in human and animal health areas and in agriculture.

The disease or group of diseases described generally as heminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oestrophagostomum, Chabertia, Trichuris, Strongylus, Trichonema, Dictoycaulus, Capillaria, Heterakis, Toxacara, Ascaridia, Oxyuris, Ancylostoma, Uncinaria, Toxascaris and Paracaris. Certian of these, such as Nematodirus, Cooperia, and Oesphagostomum primarily attack the intestinal tract while others, such as Haemonchus and Ostertagia, are most prevalent in the stomach. Still other such as Dictyocaulus are found in the lungs. Also, other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs, and if left untreated, may result in death of the infected host. The 23-oxo or -imino derivatives of the LL-F28249 compounds of this invention unexpectedly have high activity against these parasites. Additionally, they also are active against Dirofilaria in dogs, Nematospiroides, Syphacia, Aspiculuris in rodents, arthropod ectoparasites such as ticks, mites, lice, fleas, blowfly of animals and birds, the ectoparsite Lucilia sp. of sheep, biting insects and migrating dipterous larvae such as Hypoderma sp. in cattle, Gastrophilus in horses and Cuterebra sp. in rodents.

The compounds of the present invention also are useful in treating, preventing or controlling parasites which infect human beings, as well. The most common genera of parasites of the gastrointestinal tract of man are Ancylostoma, Necator, Ascaris, Strongyloides, Trichinella, Capillaria, Trichuris, and Enterobius. Other medically inmportant genera of parasites which are found in the blood or other tissues and organs outside the gastrointestinal tract are the filiarial worms such as Wuchereria, Brugia, Onchocerca and Loa, Dracunclulus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola spl., carpet beetle Attagenus sp., and the housefly Musca domestica.

Insect pests of stored grains such as Tribolium sp., Tenebrio sp., and of agricultural plants such as spider mites (Tetranycus sp.), southern army worms, tobacco budworms, boll weevils, aphids (Acyrthiosiphon sp.), migratory orthopterans such as locusts and immature stages of insects living on plant tissue are controlled by the present compounds as well as the control of soil nematodes and plant parasites such as Meloidogyne sp., which may be of importance in agriculture.

The compounds of the present invention may be administered orally or parenterally for animal and human usage, while they may be formulated in liquid or solid form for agricultural use. Oral administration may take the form of a unit dosage form such as a capsule, bolus or tablet, or as a liquid drench where used as an anthelmintic for animals.

The animal drench is normally a solution, suspension or dispersion of the active compound, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight.

Capsules and boluses comprise the active ingredient admixed with a carrier vehicle such as starch, talc, magnesium stearate or di-calcium phosphate.

Where it is desired to administer the 23-oxo or 23-imino derivatives of LL-F28249 in a dry, solid unit dosage form, capsules, boluses or tablets containing the desired amount of active compounds usually are employed. These dosage forms are prepared by intimately and uniformly mixing the active ingredient with suitable finely divided diluents, fillers, disintegrating agents and/or binders such as starch, lactose, talc, magnesium stearate, vegtable gums and the like. Such unit dosage formulations may be varied widely with respect to their total weight and content of the active compound depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the present invention may be administered to animals parenterally, such as by intraruminal, intramuscular, intratracheal, or subcutaneous injection. In such an event, the active compound is dissolved or dispersed in a liquid carrier vehicle.

For parenteral administration, the active compound is suitable admixed with an acceptable vehicle, preferably of the vegetable oil variety such as peanut oil, cotton seed oil and the like. Other parenteral vehicles such as organic preparations using solketal, propylene glycol, glycerol formal, and aqueous parenteral formulation also are used. The active 23-oxo or -imino compound or compounds of the present invention are dissolved or suspended in the parenteral formulation for administration. Such formulations generally contain about 0.005% to 5%, by weight, of the active compound.

Although the compounds of the present invention are primarily uses in the treatment, prevention or control of helminthiasis, they also are useful in the prevention and treatment of diseases caused by other parasites. For example, arthropod parasites such as ticks, lice, fleas, mites and other biting insects in domesticated animals and poultry are controlled by the present compounds. These compounds also are effective in treatment of parasitic diseases that occur in other animals including human beings. The optimum amount to be employed will, of course, depend upon the particular compound employed, the species of animal to be treated and the type and severity of parasitic infection or infestation. Generally, the amount useful in oral administration of these novel compounds is about 0.001 mg to 10 mg kg of animal body weight, such total dose being given at one time or in divided doses over a relativelyshort period of time (1–5) days). The preferred compounds of the invention give excellent control of such parasites in animals by administering about 0.025 mg to 3 mg per kg of animal body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the animal's feed, or dissolved or suspended in the drinking water, compositions are provided in which the active compound or compounds are intimately dispersed in an inert carrier or diluent. An inert carrier is one that will not react with the active component and that will be administered safely to animals. Preferebly, a carrier for feed administration is one that is, or may be, an ingredient of the animal ration.

Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grints, crushed limestone and the like. The active compounds are intimately dispersed throughout the carrier by methods such as grinding, stirring, milling or tumbling. Compositions containing about 0.005% to 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment, prevention and/or control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds also may be administered by pouring on the skin of animals via a solution. Generally, the active compounds are dissolved in a suitable inert solvent, such as dimethylsulfoxide, propylene glycol of the like, alternatively in combination of solvents, for the pour-on administration.

The compounds of this invention also are useful in combating agricultural pests that inflict damage upon growing or stored crops. The present compounds are applied, using known techniques such as sprays, dusts, emulsions and the like, to the growing or stored crops to effect protection from such agricultural pests. The present invention is illustrated by the following examples which are illustrative of said invention and not limitative thereof.

EXAMPLE 1

5-O-t-Butyldimethylsilyl-LL-F28249β

In 500 mL of $CH_2Cl_2$, 70 g of LL-F28249α is stirred with 82.04 g of imidazole at 20° C. under $N_2$ atmosphere. Then, 43 g of t-butyldimethylsilyl chloride in 400 mL of $CH_2Cl_2$ is added over 5 minutes. After an hour, the reaction is assayed for completion by high performance liquid chromatography (HPLC), using 50% $CH_3CN$/50% $H_2O$ in a curved gradient mode over 10 minutes on a Whatman Partisil $CCS/C_8$ rapid analysis column at 1 mL/min flowrate. Another 3 g of t-butyldimethylsilyl chloride is added, and after 3 hours the composition is 92.3% product, 0.3% LL-F28249α and 1.16% disilylated material. The mixture is diluted with $CH_2Cl_2$ and poured into 2L of $H_2O$. The $CH_2Cl_2$ layer is separated. The aqueous portion is extracted with 2L of $CH_2Cl_2$, and the combined organic layers are dried ($Na_2SO_4$). The $CH_2Cl_2$ is evaporated in vacuo to afford 116 g of the title compound that is identified by mass spectrometry and nuclear magnetic resonance (NMR) spectrometry.

EXAMPLE 2

5-O-t-Butyldimethylsilyl-23-oxo-LL-F28249α

In 5L of dry $Ch_2Cl_2$, 116 g of 5-O-t-butyldimethylsilyl LL-F28249α is stirred under $N_2$, and 540 g of NaOAc is added at 22° C., followed by addition of 172.5 g of pyridinium chlorochromate (PCC). After 1 hour, an additional 15 g of PCC is added since the reaction is incomplete by HPLC analysis. After 2 hours, another 10 g of PCC is added, and the reaction is stirred for a total of 5 hours. The mixture is poured into 6L of ice-water mixture, and the $CH_2Cl_2$ is separated. The aqueous layer is extracted with $CH_2Cl_2$, and the combined $CH_2Cl_2$ layers are washed with water and dried ($Na_2SO_4$). The $CH_2Cl_2$ is evaporated in vacuo to afford 197.8 g of crude product, which is dissolved in 2L or $Et_2O$ and filtered. The $Et_2O$ solution is washed with water (2×1000 mL), dried ($Na_2SO_4$) and evaporated to dryness to give 60 g of the title compound which is identified by mass spectrometry and NMR spectroscopy.

The pyridinium chlorochromate substituted with pyridinium dichromate in the above procedure also affords the title compound.

EXAMPLE 3

23-Oxo-LL-F28249α

In 1.5L of MeOH, 60 g of 5-t-butyldimethyl-silyl-23-oxo-LL-F28249α is dissolved by warming, and at 0° C., 30 g of p-toluenesulfonic acid in 300 mL of MeOH is added. The mixture is stirred for 3 hours and poured into 6L of saturated $NaHCO_3$ solution in 6L of $H_2O$. After stirring, the mixture is extracted with 4 L of EtOAc, and the layers are separate. The aqueous layer is saturated with NaCl and extracted with 2×6 L of EtOAc. The first EtOAc layer is washed with saturated NaCl solution, combined with the other EtOAc extracts and dried ($Na_2SO_4$). The EtOAc is evaporated in vacuo to afford 148.1 g of dark residue. The crude material is then chromatographed by HPLC on 1200 g of SiO$_2$ using 1% isopropanol in CH$_2$Cl$_2$ to elute and monitored by an ultraviolet detector/254 nM filter. Fractions 39-42 are combined and evaporated to dryness to afford 12.65 g of the title compound which analyzes as follows:

Anal. Calcd for C$_{36}$H$_{50}$O$_8$: C,70.79; H, 8.25. Found: C, 70.33; H, 8.31.

The title compound is further identified by mass spectrometry and NMR spectroscopy.

EXAMPLES 4 AND 5

23-O-Methyloxime-LL-F28249α

In 930 mL of dry dioxane at room temperature, 70 g of 23-oxo-LL-F28249α, 11.8 g of NaOAc, 11.8 g of CH$_3$ONH$_2$·HCl and 2.1 mL of HOAc are added. The mixture is stirred under N$_2$ for 3 days, and after no starting material is detected by HPLC, 650 mL of dioxane is evaporated in vacuo. The residue is poured into 5 L of H$_2$O, and the product is extracted with CH$_2$Cl$_2$ (4×2L). The combined extracts are washed with H$_2$O, dried (Na$_2$SO$_4$) and evaporated to dryness. The residue is dissolved in 1500 mL of Et$_2$O, and the solution is washed with H$_2$O, dried (Na$_2$SO$_4$) and evaporated to dryness. This gives 11.84 g of the title compound, which is identified by mass spectrometry and NMR spectroscopy. It also analyzes as follows:

Anal. Calcd for C$_{37}$H$_{53}$O$_8$N.1.5 H$_2$O: C, 66.64; H, 8.46; N, 2.10. Found: C, 66.82; H, 8.13; N, 2.32.

The title compound is acetylated with excess acetic anhydride in methylene chloride at room temperature to afford 5-acetyl-23-O-methyloxime-LL-F28249α, which is identified by mass spectrometry and NMR spectroscopy after chromatographic purification.

EXAMPLE 6

23-Oxime-LL-F28249α

In 5 mL of dioxane, 62 mg of 23-oxo-LL-F28249α is stirred with 49 mg of NH$_2$OH·HCl, 50 mg of NaOAc and 10 μl of HOAc for 23 hours under N$_2$ atmosphere. The mixture is poured into 250 mL each of H$_2$O and CH$_2$Cl$_2$, and the CH$_2$Cl$_2$ layer is separated. The aqueous layer is extracted with 50 mL of CH$_2$Cl$_2$, and the combined CH$_2$Cl$_2$ solutions are washed with H$_2$O, dried (Na$_2$SO$_4$) and evaporated to dryness to afford 8.8 mg of residue. This material is purified on a preparative layer plate (silica gel) using 20, MeOH in CH$_2$Cl$_2$ to afford the title compound which is identified by mass spectrometry and NMR spectroscopy.

EXAMPLE 7

23-[O-(Methylcarbamoyl)oxime]-LL-F28249α

In 5 mL of Et$_2$O, 27.2 mg of 23-oxime-LL-F28249α is stirred under N$_2$ with 10 μl of Et$_3$N and 50 μL of methyl isocyanate for 17 hours at room temperature. The ether is evaporated, and the residue is purified on a preparative chromatography plate (silica gel) using 20% MeOH in CH$_2$Cl$_2$ to afford the title compound, which is identified by mass spectrometry and NMR spectroscopy.

EXAMPLES 8-20

The following 23-O-substituted oxime-LL-F28249α compounds are prepared by the method of Example 4 using the appropriate O-substituted hydroxylamines in place of methoxyamine:

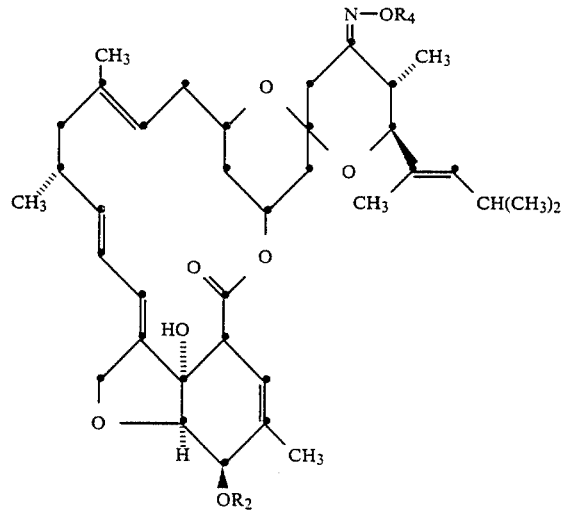

| R$_2$ | R$_4$ |
| --- | --- |
| H | Ethyl |
| H | n-Hexyl |
| H | i-Propyl |
| H | Benzyl |
| H | Phenyl |
| H | Allyl |
| H | Propargyl |
| H | CH$_2$COO-t-Butyl |
| H | CH$_2$COO-Ethyl |
| CH$_3$ | Ethyl |
| CH$_3$ | Benzyl |
| CH$_3$CO | Ethyl |
| ClCH$_2$CO | Ethyl |

EXAMPLE 21

2-O-t-Butyldimethylsilyl-23-oxime-LL-F28249α

In the manner described in Example 5, 5-O-t-butyldimethylsilyl-23-oxime-LL-F28249α is prepared and purified by chromatography over silica gel.

EXAMPLES 22-32

23-[O-Substituted-carbamoyl)oxime]-LL-F28249α

The following 23-O-substituted-carbamoyl)-oximes of LL-F28249α are prepared by the method of Example 7 by using the appropriate isocyanates:

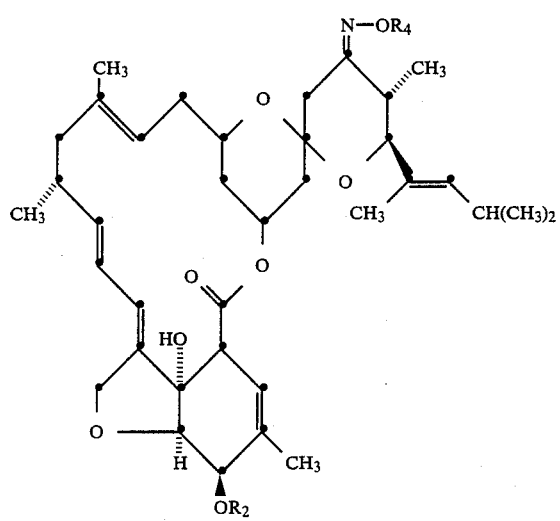

| R₂ | R₄ |
|---|---|
| H | $C_2H_5NH-CO$ |
| H | $n-C_6H_{13}NH-CO$ |
| H | $i-C_3H_7NH-CO$ |
| H | Benzyl-NH—CO |
| H | Phenyl-NH—CO |
| H | 4-Chlorophenyl-NH—CO |
| H | Allyl-NH—CO |
| H | Propargyl-NH—CO |
| $CH_3$ | $C_2H_5NH-CO$ |
| $CH_3$ | Benzyl-NH—CO |
| H | 3,4-Dichlorophenyl-NHCO |

EXAMPLES 33

23-[O-Acetyl)oxime]-LL-F28249α

In 1 mL of $CH_2Cl_2$, 60 mg of 23-oxime-LL-F28249α is stirred with 6 μL of triethylamine at 0° C., and 5 mL of a solution containing 244.4 mg of acetic anhydride in 100 mL of $CH_2Cl_2$ is added. The reaction mixture is stirred at 0° C. for 24 hours and evaporated to dryness in vacuo. The residue is dissolved in 50 mL of $CH_2Cl_2$ and washed with 30 mL of $H_2O$. The solution is dried ($Na_2SO_4$) and evaporated to dryness to afford 53.2 mg of the title compound, which is identified by NMR spectroscopy and mass spectrometry.

EXAMPLE 34–41

By the procedure of Example 33, the following 23-[0-(substituted)oximes] of LL-28249 are prepared by using the appropriate acid anhydrides.

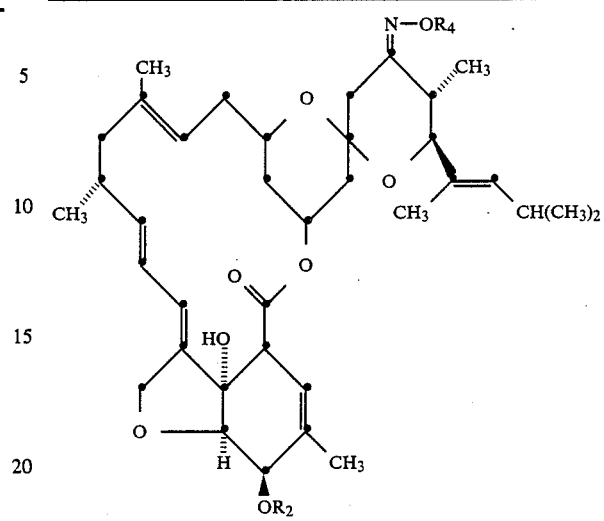

| R₂ | R₄ |
|---|---|
| H | $ClCH_2CO$ |
| H | $CH_3OCH_2CO$ |
| H | $n-C_4H_9CO$ |
| H | $i-C_4H_9CO$ |
| H | $C_6H_5CO$ |
| H | $C_6H_5CH_2CO$ |
| $CH_3$ | $CH_3OCH_2CO$ |
| H | Phenylacetyl |
| H | $C_6H_5OCH_2CO$ |

EXAMPLES 42

5-0-Acetyl-23-Oxo-LL-F28249α

In 2.5 mL of $CH_2Cl_2$, 61 mg of 23-oxo-LL-F28249α is stirred with 49 mg of 4-dimethylaminopyridine, and 52 mg of diisopropylethylamine and 32 mg of acetyl chloride in 1 mL of $CH_2Cl_2$ is added at 0° C. The mixture is stirred at 0°–5° C. for 1.5 hours and poured into ice/$H_2O$, and the aqueous mixture is made acidic with 1:1 aqueous HCl. The mixture is then extracted with 3×2 mL of $CH_2Cl_2$, and the extracts are dried ($MgSO_4$) and evaporated to dryness. The crude product is dissolved in acetone and applied on a preparative silica gel plate and chromatographed in 20 $CH_2Cl_2$/1 EtOAc (vol/vol). The title compound is recovered by extraction with 10% MeOH in $CH_2Cl_2$ and identified by mass spectrometry and NMR spectroscopy.

EXAMPLE 43

5-0-Acetyl-23-methoxime-LL-F28249α

In the manner described in Example 4 and 5, 5-0-acetyl-23-oxo-LL-F28249α is reacted with $MeONH_2.HCl$ to afford the title compound, which is identified by mass spectrometry and NMR spectroscopy.

EXAMPLES 44–50

5-0-Acyl-23-oxo-LL-F28249α

Using the procedure of Example 42, the following 5-0-acyl-23-oxo-LL-F28249α compounds are prepared using the requisite acid chlorides.

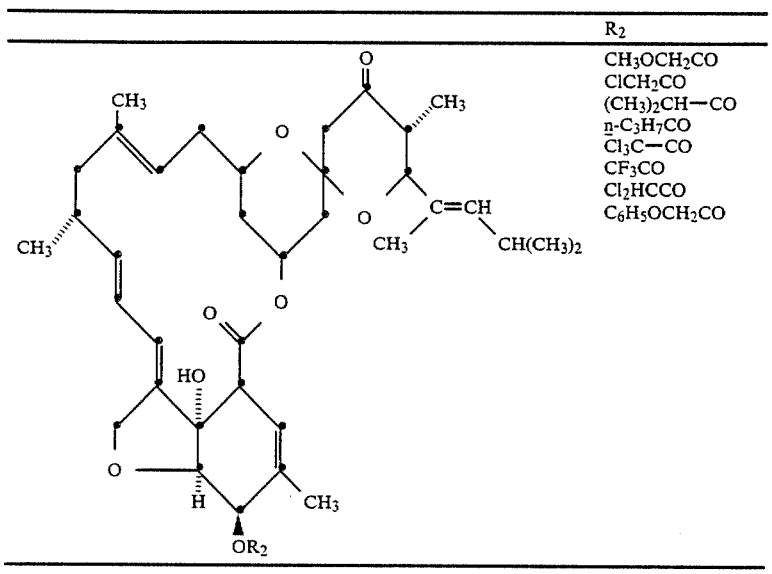

| | $R_2$ |
|---|---|
| | $CH_3OCH_2CO$ |
| | $ClCH_2CO$ |
| | $(CH_3)_2CH-CO$ |
| | $n-C_3H_7CO$ |
| | $Cl_3C-CO$ |
| | $CF_3CO$ |
| | $Cl_2HCCO$ |
| | $C_6H_5OCH_2CO$ |

EXAMPLES 51–57

5-0-Acyl-23-0-Substituted-oxime-LL-F28249α

By the procedure of Examples 4 and 5, the following oximes are prepared by reacting the 5-0-acyl-23-oxo-LL-F28249α with the appropriate 0-substituted hydroxylamine.

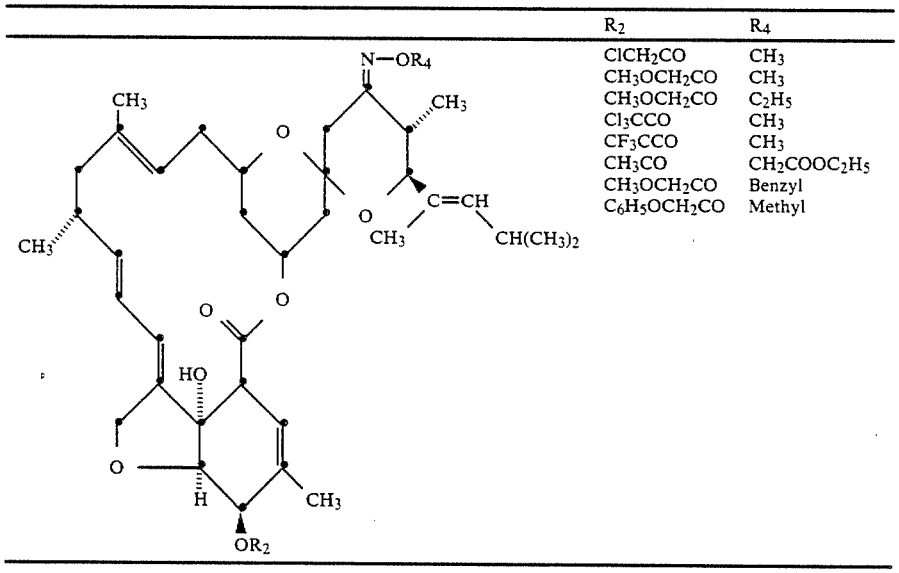

| | $R_2$ | $R_4$ |
|---|---|---|
| | $ClCH_2CO$ | $CH_3$ |
| | $CH_3OCH_2CO$ | $CH_3$ |
| | $CH_3OCH_2CO$ | $C_2H_5$ |
| | $Cl_3CCO$ | $CH_3$ |
| | $CF_3CCO$ | $CH_3$ |
| | $CH_3CO$ | $CH_2COOC_2H_5$ |
| | $CH_3OCH_2CO$ | Benzyl |
| | $C_6H_5OCH_2CO$ | Methyl |

EXAMPLE 58

23-Oxo-LL-F28249α

A solution containing 0.32 g of oxalyl chloride in 5 mL of $CH_2Cl_2$ is cooled and stirred with 0.71 g of Type 4A molecular sieves in a dry-ice/acetone bath, and a mixture of 0.4 g of dimethylsulfoxide (DMSO) in 2 mL of $CH_2Cl_2$ is added slowly with stirring under $N_2$ atmosphere. Subsequently, 0.83 g of 5-0-t-butyldimethylsilyl-LL-F28249α in 8 mL of $CH_2Cl_2$ is added dropwise over 10 minutes. After 0.5 hours, 1.6 mL of triethylamine is added dropwise, and the mixture is allowed to rise to room temperature (about 25° C.) over an hour. The mixture is poured into an ice-$H_2O$ mixture, and the aqueous mixture is extracted with 3×10 mL of $Et_2O$. The $Et_2O$ layers are washed with $H_2O$ (5×5 mL) and dried ($MgSo_4$). Ether is removed, and the residue is dissolved in 15 mL of MeOH. The MeOH solution is stirred at 0° C. with 0.3 g p-toluenesulfonic acid for 3 hour and poured into 60 mL of saturated $NaHCO_3$ and 60 mL of $H_2O$. The aqueous mixture is stirred with NaCl until it is saturated and extracted with EtOAc (3×40 mL). The combined EtOAc layers are dried ($MgSO_4$) and evaporated to dryness to afford the title compound that is identical with the material obtained by the method of Example 3.

EXAMPLE 59

23-Oxo-LL-F28249λ

Using the procedure of Example 2, LL-F28249λ is converted to the title compound 23-oxo-LL-F28249λ, which is purified by chromatography on silica gel and

EXAMPLES 60–61

23-Oxo-LL-F28249β

By the procedure of Example 1, LL-F28249β is protected with 5-t-butyldimethylsilyl chloride, and the protected product is oxidized in manner described in Example 2. Deprotection of the 5-silyl group is accomplished by the procedure of Example 3 to afford the title compound which is identified by mass spectrometry and NMR spectroscopy.

Similar 23-oxo-LL-F28249λ is prepared from LL-F28249λ.

EXAMPLE 62

23-Semicarbazone-LL-F28249α

In 6 mL of dry dioxane under $N_2$ atmosphere, 60 mg of 23-oxo-LL-F28249α is stirred with 56.4 mg of NaOAc, 77 mg of semicarbazide hydrochloride and 18 μL of HOAc for 6 days at room temperature. The mixture is poured on ice and mixed with 100 mL each of $H_2O$ and $CH_2Cl_2$. The $CH_2Cl_2$ layer is separated, and the aqueous layer is extracted with 50 mL of $CH_2Cl_2$. The combined extracts are washed with 75 mL of $H_2O$ and evaporated to dryness. The residue is dissolved in 100 mL of $Et_2O$, and the solution is washed with $8 \times 50$ mL of $H_2O$, dried ($Na_2SO_4$) and evaporated to dryness to afford 47.5 mg of the title compound.

EXAMPLES 63–68

In the same manner the following semicarbazones and thiosemicarbazone compounds are prepared by the procedure of Example 62.

| | Y | $R_6$ | $R_7$ |
|---|---|---|---|
| | S | H | H |
| | S | $CH_3$ | $CH_3$ |
| | O | $CH_3$ | H |
| | O | $CH_3$ | $CH_3$ |
| | O | $n\text{-}C_4H_9$ | H |
| | O | $i\text{-}C_3H_7$ | H |
| | O | $C_6H_5$ | H |
| | *S | $C_6H_5$ | H |

* = methanol used as solvent in this preparation

EXAMPLES 69–73

23-(2-Carbomethoxyhydrazone)-LL-F28249α

In 15 mL of MeOH, 50 mg of 23-oxo-LL-F28249α is stirred with 25 mg of methyl carbazate in the presence of 10 μL of HOAc. After 3 days, the mixture is poured on ice and diluted with $H_2O$. The aqueous phase is saturated with salt and extracted with $CH_2Cl_2$ several times. The $CH_2Cl_2$ extracts are dried ($Na_2SO_4$) and evaporated to dryness. The residue is purified by chromatography on silica gel using 2% isopropanol in $CH_2Cl_2$ as eluent to afford the title compound.

Similarly the 2-carbethoxyhydrazone and 2-carbobutoxyhydrazones are prepared using the appropriate carbazates. Also, 1-methylhydrazine is similarly reacted with the above ketone to afford 23-(1-methylhydrazone)-LL-F28249α, while use of acethydrazide affords 23-acethydrazone-LL-F28249α.

Following the above procedure but substituting formic acid hydrazide for semicarbazide hydrochloride yields 23-(formylhydrazone)-F28249α in the form of a white solid.

EXAMPLE 74

23-[O-(ethoxymethyl)oxime]-F28249α

A suspension of 40 mg 23-oximino-LL-F28249α, 30.2 mg chloromethylethylether, 44.2 mg potassium carbonate and 2 mL DMF is stirred at room temperature for 36 hours. The mixture is diluted with water and extracted twice with 50 mL of ether. The combined ether layers are washed with 50 mL of water and 50 mL of brine, dried ($MgSO_4$), and evaporated. The residue is purified by chromatography on silica gel using 1.0 to 1.5% isopropanol an $CH_2Cl_2$ as eluent to afford the title compound in the form of a white glass.

EXAMPLE 75

23-[(p-tolylsulfonyl)hydrazone]-F28249α

A solution of 25.5 mg of 23-oxo-LL-F28249α, 7.7 mg of toluenesulfonylhydrazine and 1 mL ethanol is at reflux for 30 minutes. An additional 5.0 mg of the hydrazone is added and heating continued for an additional 30 minutes. The mixture is diluted with 5 mL of ether and is extracted with 2 mL of $H_2O$ followed by 1 mL of brine containing 3 drops of acetic acid. The combined aqueous layers are washed with 3 mL of ether. The combined ether solutions are dried ($MgSO_4$) and evaporated. The residue is purified by silica gel chromatography on silica gel using 1.5% isopropanol in $CH_2Cl_2$ as the eluent to afford the title compound in the form of a white glass.

EXAMPLE 76

23-tetrafluorophenylhydrazone-LL-F28249α

In 8 mL of methanol under $N_2$ atmosphere, 80 mg of 23-oxo-LL-F28249α is stirred with 80 mg of pentafluorophenylhydrazine and 16 μl of HOAc for 5 hours at room temperature. The mixture was diluted with 200 mL of $CH_2Cl_2$ and washed twice with 200 mL of 5% HCl. The aqueous extracts were combined and reextracted twice with 300 mL of $CH_2Cl_2$. The $CH_2Cl_2$ extracts were combined and with 100 mL of saturated $NaHCO_3$, dried ($NaSO_4$), filtered and evaporated. The residue is purified by chromatography on silica gel using 1% isopropanol in $CH_2Cl_2$ as eluent to afford the title compound having a melting point of 142° C.

EXAMPLE 77

23-oxamic acid hydrazone-LL-F28249α

In 15 mL of refluxing EtOH under $N_2$ atmosphere, 80 mg of 23-oxo-LL-F28249α is stirred with 45 mg oxamic acid hydrazide for 3 days. The mixture is diluted with 200 mL $CH_2Cl_2$ and washed twice with 200 mL 5% HCl. The combined aqueous extract were reextracted twice with 300 mL $CH_2Cl_2$. The combined $CH_2Cl_2$ extracts were combined, washed with 100 mL saturated $NaHCO_3$ dried ($Na_2SO_4$), filtered, and evaporated. The residue is purified by chromatography on silica gel using 2% isopropanol in $CH_2Cl_2$ as eluent to afford the title compound. m.p. 175° (decomp).

What is claimed is:

1. A compound represented by structural formula (I):

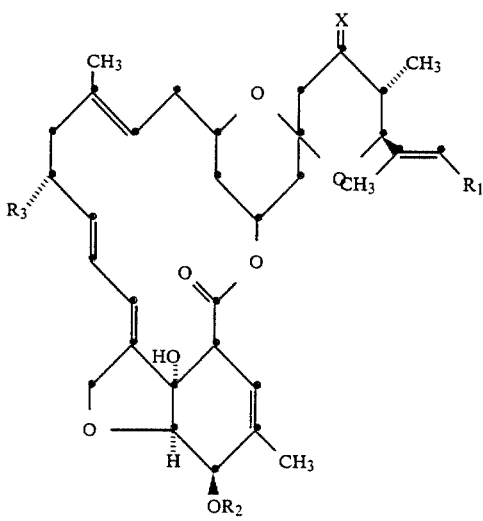

wherein R₁ is methyl, ethyl or isopropyl; R₂ is hydrogen, methyl, $C_1$–$C_4$ alkanoyl, methoxyacetyl, chloroacetyl, dichloroacetyl, trichloroacetyl, trifluoroacetyl, phenoxyacetyl, optionally substituted on the phenyl ring with one or two halogens, $C_1$–$C_4$ alkyl groups, $C_1$–$C_4$ alkoxy groups or nitro groups, or benzoyl optionally substituted with one or two halogens, $C_1$–$C_4$ alkyl groups, $C_1$–$C_4$ alkoxy groups, or nitro groups; $R_3$ is hydrogen or methyl; X is $NOR_4$, or $N-NHR_5$; $R_4$ is hydrogen, $C_1$–$C_6$ alkyl, $C_1$–$C_4$ alkoxymethyl, benzyl, allyl, propargyl, phenyl, $CH_2COO$-alkyl ($C_1$–$C_4$), N-($C_1$–$C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$–$C_6$ alkanoyl, chloroacetyl, methoxyacetyl, phenylacetyl optionally substituted on the phenyl ring with one or two halogens, $C_1$–$C_4$ alkyl groups, $C_1$–$C_4$ alkoxy groups or nitro groups, phenoxyacetyl optionally substituted on the phenyl ring by one or two halogens, $C_1$–$C_4$ alkyl groups, $C_1$–$C_4$ alkoxy groups or nitro groups, or benzoyl optionally substituted with one or two halogens, $C_1$–$C_4$ alkyl groups, $C_1$–$C_4$ alkoxy groups or nitro groups; $R_5$ is

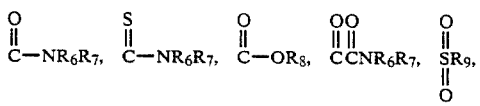

$C_1$–$C_6$ alkanoyl, $C_1$–$C_6$ alkyl,

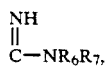

or benzoyl optionally substituted with one or two halogens, $C_1$–$C_4$ alkyl groups, $C_1$–$C_4$ alkoxy groups or nitro groups; $R_6$ and $R_7$ are hydrogen or $C_1$–$C_6$ alkyl, or phenyl optionally substituted with one or two halogens, $C_1$–$C_4$ alkyl, $C_1$–$C_4$ alkoxy, or phenyl optionally substituted with one or two halogens, $C_1$–$C_4$ alkyl groups, $C_1$–$C_4$ alkoxy groups or nitro groups, $R_8$ is $C_1$–$C_6$ alkyl or phenyl optionally substituted with one or two halogens, $C_1$–$C_4$ alkyl groups, $C_1$–$C_4$ alkoxy groups or nitro groups; $R_9$ is $C_1$–$C_6$ alkyl or phenyl optionally substituted with one or two halogens, $C_1$–$C_4$ alkyl groups, $C_1$–$C_4$ alkoxy groups or nitro groups; or a pharmaceutically and pharmacologically acceptable salt thereof.

2. The compound according to claim 1, wherein $R_1$ is isopropyl; $R_2$ is hydrogen or methyl; $R_3$ is methyl; and X is $NOR_4$, $N-NHCH_3$,

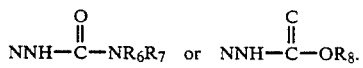

3. The compound according to claim 1, wherein $R_1$ is isopropyl; $R_2$ is hydrogen; $R_3$ is methyl; X is $NOR_4$, $N-NHCH_3$, or

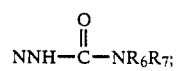

and $R_4$ is $C_1$–$C_3$ alkyl, N-($C_1$–$C_6$ alkyl)carbamoyl, N-(allyl)carbamoyl, N-(propargyl)carbamoyl, N-(phenyl)carbamoyl, N-(4-chlorophenyl)carbamoyl, N-(benzyl)carbamoyl, $C_1$–$C_6$ alkanoyl, chloroacetyl, methoxyacetyl, benzoyl or chlorobenzoyl and $R_6$ and $R_7$ are as described in said claim 1.

4. The compound according to claim 1, wherein $R_1$ is isopropyl; $R_2$ is hydrogen; $R_3$ is methyl; X is $NOR_4$, or

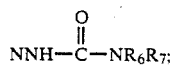

and $R_4$ is methyl, ethyl, N-($C_1$–$C_4$ alkyl)carbamoyl, N-(phenyl)carbamoyl, or N-(4-chlorophenyl)carbamoyl.

5. The compound according to claim 2, wherein $R_1$ is isopropyl; $R_2$ is hydrogen; $R_3$ is methyl; and X is $NOCH_3$.

6. The compound according to claim 2, wherein $R_1$ is isopropyl; $R_2$ is hydrogen; $R_3$ is methyl; and X is

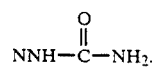

7. A method for the prevention, treatment or control of endoparasitic or ectoparasitic infections in warm-blooded animals, said method comprising: orally, topically or parenterally administering to an animal infected with endo- or ectoparasites, an endo- or ectoparasiticidally effective amount of a compound represented by structural formula (I),

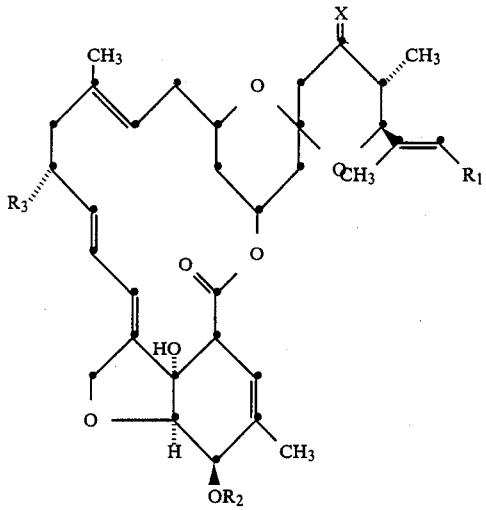

wherein $R_1$ is methyl, ethyl or isopropyl; $R_2$ is hydrogen, methyl, $C_1$–$C_4$ alkanoyl, methoxyacetyl, chloroacetyl, dichloroacetyl, trichloroacetyl, trifluoroacetyl, phenoxyacetyl, optionally substituted on the phenyl ring with one or two halogens, $C_1$–$C_4$ alkyl groups, $C_1$–$C_4$ alkoxy groups or nitro groups, or benzoyl optionally substituted with one or two halogens, $C_1$–$C_4$ alkyl groups, $C_1$–$C_4$ alkoxy groups, or nitro groups; $R_3$ is hydrogen or methyl; X is $NOR_4$, or N—$NHR_5$; $R_4$ is hydrogen, $C_1$–$C_6$ alkyl, $C_1$–$C_4$ alkoxymethyl, benzyl, allyl, propargyl, phenyl, $CH_2COO$-alkyl ($C_1$–$C_4$), N-($C_1$–$C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$–$C_6$ alkanoyl, chloroacetyl, methoxyacetyl, phenylacetyl optionally substituted on the phenyl ring with one or two halogens, $C_1$–$C_4$ alkyl groups, $C_1$–$C_4$ alkoxy groups or nitro groups, phenoxyacetyl optionally substituted on the phenyl ring by one or two halogens, $C_1$–$C_4$ alkyl groups, $C_1$–$C_4$ alkoxy groups or nitro groups, or benzoyl optionally substituted with one or two halogens, $C_1$–$C_4$ alkyl groups, $C_1$–$C_4$ alkoxy groups or nitro groups; $R_5$ is

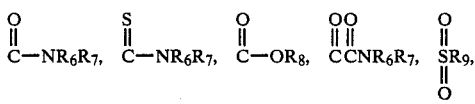

$C_1$–$C_6$ alkanoyl, $C_1$–$C_6$ alkyl,

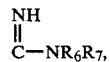

or benzoyl optionally substituted with one or two halogens, $C_1$–$C_4$ alkyl groups, $C_1$–$C_4$ alkoxy groups or nitro groups; $R_6$ and $R_7$ are hydrogen or $C_1$–$C_6$ alkyl, or phenyl optionally substituted with one or two halogens, $C_1$–$C_4$ alkyl, $C_1$–$C_4$ alkoxy, or phenyl optionally substituted with one or two halogens, $C_1$–$C_4$ alkyl groups, $C_1$–$C_4$ alkoxy groups or nitro groups, $R_8$ is $C_1$–$C_6$ alkyl or phenyl optionally substituted with one or two halogens, $C_1$–$C_4$ alkyl groups, $C_1$–$C_4$ alkoxy groups or nitro groups; $R_9$ is $C_1$–$C_6$ alkyl or phenyl optionally substituted with one or two halogens, $C_1$–$C_4$ alkyl groups, $C_1$–$C_4$ alkoxy groups or nitro groups; or a pharmaceutically and pharmacologically acceptable salt thereof.

8. A method according to claim 7, wherein said compound has $R_1$ as isopropyl; $R_2$ as hydrogen or methyl; $R_3$ as methyl; and X as $NOR_4$, N—$NHCH_3$,

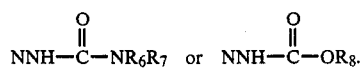

9. A method according to claim 8, wherein said compound has $R_1$ as isopropyl; $R_2$ as hydrogen; $R_3$ as methyl; and X as $NOCH_3$.

10. A method according to claim 8, wherein said compound has $R_1$ as isopropyl; $R_2$ as hydrogen; $R_3$ as methyl; and X as

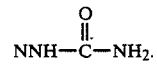

11. A method for protecting crops, trees, shrubs, stored grain and ornamentals from attack by acarids or insects which infest them, said method comprising: applying an acaricidally or insecticidally-effective amount of a compound represented by structural formula (I),

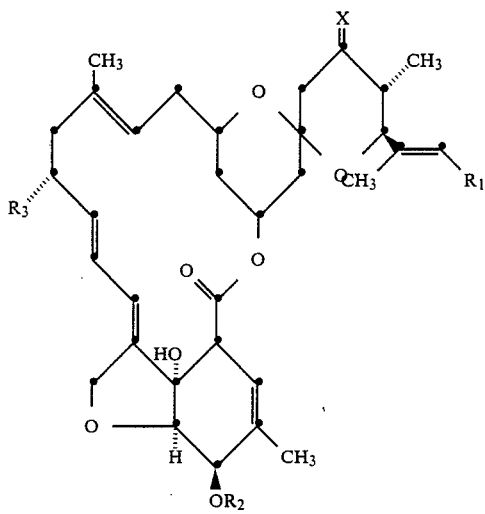

wherein $R_1$ is methyl, ethyl or isopropyl; $R_2$ is hydrogen, methyl, $C_1$–$C_4$ alkanoyl, methoxyacetyl, chloroacetyl, dichloroacetyl, trichloroacetyl, trifluoroacetyl, phenoxyacetyl, optionally substituted on the phenyl ring with one or two halogens, $C_1$–$C_4$ alkyl groups, $C_1$–$C_4$ alkoxy groups or nitro groups, or benzoyl optionally substituted with one or two halogens, $C_1$–$C_4$ alkyl groups, $C_1$–$C_4$ alkoxy groups, or nitro groups; $R_3$ is hydrogen or methyl; X is $NOR_4$, or N—$NHR_5$; $R_4$ is hydrogen, $C_1$–$C_6$ alkyl, $C_1$–$C_4$ alkoxymethyl, benzyl, allyl, propargyl, phenyl, $CH_2COO$-alkyl ($C_1$–$C_4$), N-($C_1$–$C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$–$C_6$ alkanoyl, chloroacetyl, methoxyacetyl, phenylacetyl optionally substituted on the phenyl ring with one or two halogens, $C_1$–$C_4$ alkyl groups, $C_1$–$C_4$ alkoxy groups or nitro groups, phenoxyacetyl optionally substituted on the phenyl ring by one or two halogens, $C_1$-$C_4$ alkyl groups, $C_1$-$C_4$ alkoxy groups or nitro groups, or benzoyl optionally substituted with one or two halogens, $C_1$-$C_4$ alkyl groups, $C_1$-$C_4$ alkoxy groups or nitro groups; $R_5$ is

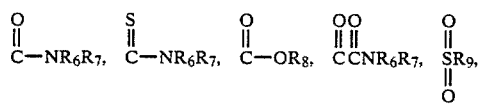

$C_1$-$C_6$ alkanoyl, $C_1$-$C_6$ alkyl,

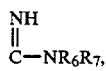

or benzoyl optionally substituted with one or two halogens, $C_1$-$C_4$ alkyl groups, $C_1$-$C_4$ alkoxy groups or nitro groups; $R_6$ and $R_7$ are hydrogen or $C_1$-$C_6$ alkyl, or phenyl optionally substituted with one or two halogens, $C_1$-$C_4$ alkyl, $C_1$-$C_4$ alkoxy, or phenyl optionally substituted with one or two halogens, $C_1$-$C_4$ alkyl groups, $C_1$-$C_4$ alkoxy groups or nitro groups, $R_8$ is $C_1$-$C_6$ alkyl or phenyl optionally substituted with one or two halogens, $C_1$-$C_4$ alkyl groups, $C_1$-$C_4$ alkoxy groups or nitro groups; $R_9$ is $C_1$-$C_6$ alkyl or phenyl optionally substituted with one or two halogens, $C_1$-$C_4$ alkyl groups, $C_1$-$C_4$ alkoxy groups or nitro groups; or a pharmaceutically and pharmacologically acceptable salt thereof.

12. A method according to claim 11, wherein said compound has $R_1$ as isopropyl; $R_2$ as hydrogen; $R_3$ as methyl and X as $NOCH_3$.

13. A method for the control of plant nematodes, said method comprising: applying to the foliage of plants, the soil in which they are grown or into the trunks thereof, a nematocidally-effective amount of a compound represented by structural formula (I),

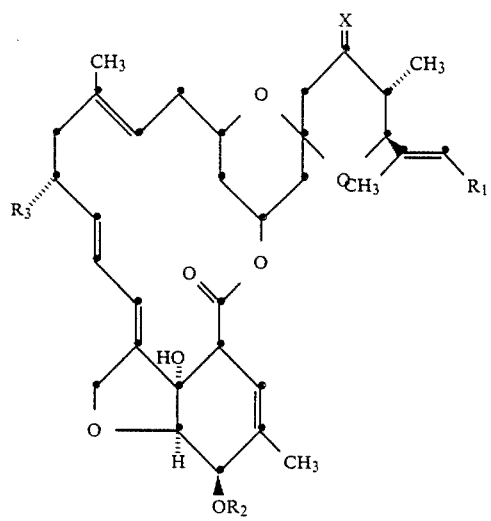

wherein $R_1$ is methyl, ethyl or isopropyl; $R_2$ is hydrogen, methyl, $C_1$-$C_4$ alkanoyl, methoxyacetyl, chloroacetyl, dichloroacetyl, trichloroacetyl, trifluoroacetyl, phenoxyacetyl, optionally substituted on the phenyl ring with one or two halogens, $C_1$-$C_4$ alkyl groups, $C_1$-$C_4$ alkoxy groups or nitro groups, or benzoyl optionally substituted with one or two halogens, $C_1$-$C_4$ alkyl groups, $C_1$-$C_4$ alkoxy groups, or nitro groups; $R_3$ is hydrogen or methyl; X is $NOR_4$, or $N-NHR_5$; $R_4$ is hydrogen, $C_1$-$C_6$ alkyl, $C_1$-$C_4$ alkoxymethyl, benzyl, allyl, propargyl, phenyl, $CH_2COO$-alkyl ($C_1$-$C_4$), N-($C_1$-$C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$-$C_6$ alkanoyl, chloroacetyl, methoxyacetyl, phenylacetyl optionally substituted on the phenyl ring with one or two halogens, $C_1$-$C_4$ alkyl groups, $C_1$-$C_4$ alkoxy groups or nitro groups, phenoxyacetyl optionally substituted on the phenyl ring by one or two halogens, $C_1$-$C_4$ alkyl groups, $C_1$-$C_4$ alkoxy groups or nitro groups, or benzoyl optionally substituted with one or two halogens, $C_1$-$C_4$ alkyl groups, $C_1$-$C_4$ alkoxy groups or nitro groups; $R_5$ is

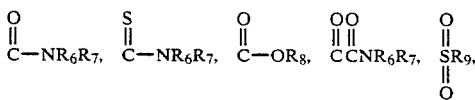

$C_1$-$C_6$ alkanoyl, $C_1$-$C_6$ alkyl,

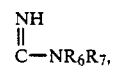

or benzoyl optionally substituted with one or two halogens, $C_1$-$C_4$ alkyl groups, $C_1$-$C_4$ alkoxy groups or nitro groups; $R_6$ and $R_7$ are hydrogen or $C_1$-$C_6$ alkyl, or phenyl optionally substituted with one or two halogens, $C_1$-$C_4$ alkyl, $C_1$-$C_4$ alkoxy, or phenyl optionally substituted with one or two halogens, $C_1$-$C_4$ alkyl groups, $C_1$-$C_4$ alkoxy groups or nitro groups, $R_8$ is $C_1$-$C_6$ alkyl or phenyl optionally substituted with one or two halogens, $C_1$-$C_4$ alkyl groups, $C_1$-$C_4$ alkoxy groups or nitro groups; $R_9$ is $C_1$-$C_6$ alkyl or phenyl optionally substituted with one or two halogens, $C_1$-$C_4$ alkyl groups, $C_1$-$C_4$ alkoxy groups or nitro groups; or a pharmaceutically and pharmacologically acceptable salt thereof.

14. A method according to claim 13, wherein said compound has $R_1$ as isopropyl; $R_2$ as hydrogen; $R_3$ as methyl; and X as $NOCH_3$.

15. A composition for treating, preventing or controlling endo- or ectoparasitic infections in warm-blooded animals or for controlling insects, said composition comprising: a pharmacologically or insecticidally-effective amount of a compound represented by structural formula (I),

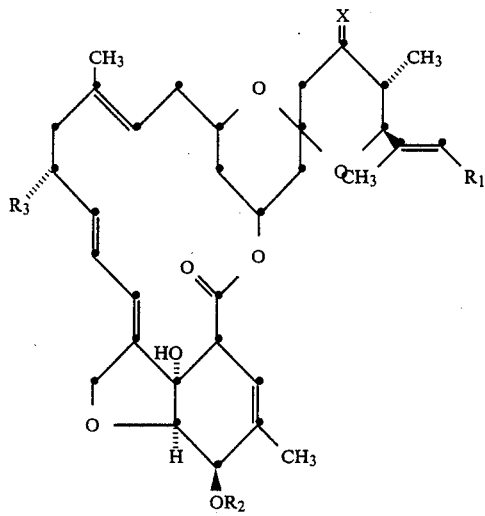

wherein $R_1$ is methyl, ethyl or isopropyl; $R_2$ is hydrogen, methyl, $C_1$-$C_4$ alkanoyl, methoxyacetyl, chloroacetyl, dichloroacetyl, trichloroacetyl, trifluoroacetyl, phenoxyacetyl, optionally substituted on the phenyl ring with one or two halogens, $C_1$-$C_4$ alkyl groups, $C_1$-$C_4$ alkoxy groups or nitro groups, or benzoyl optionally substituted with one or two halogens, $C_1$-$C_4$ alkyl groups, $C_1$-$C_4$ alkoxy groups, or nitro groups; $R_3$ is hydrogen or methyl; X is $NOR_4$, or $N$—$NHR_5$; $R_4$ is hydrogen, $C_1$-$C_6$ alkyl, $C_1$-$C_4$ alkoxymethyl, benzyl, allyl, propargyl, phenyl, $CH_2COO$-alkyl ($C_1$-$C_4$), N-($C_1$-$C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$-$C_6$ alkanoyl, chloroacetyl, methoxyacetyl, phenylacetyl optionally substituted on the phenyl ring with one or two halogens, $C_1$-$C_4$ alkyl groups, $C_1$-$C_4$ alkoxy groups or nitro groups, phenoxyacetyl optionally substituted on the phenyl ring by one or two halogens, $C_1$-$C_4$ alkyl groups, $C_1$-$C_4$ alkoxy groups or nitro groups, or benzoyl optionally substituted with one or two halogens, $C_1$-$C_4$ alkyl groups, $C_1$-$C_4$ alkoxy groups or nitro groups; $R_5$ is

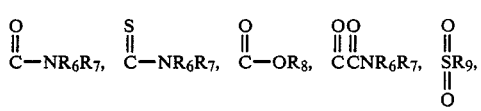

$C_1$-$C_6$ alkanoyl, $C_1$-$C_6$ alkyl,

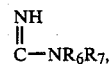

or benzoyl optionally substituted with one or two halogens, $C_1$-$C_4$ alkyl groups, $C_1$-$C_4$ alkoxy groups or nitro groups; $R_6$ and $R_7$ are hydrogen or $C_1$-$C_6$ alkyl, or phenyl optionally substituted with one or two halogens, $C_1$-$C_4$ alkyl, $C_1$-$C_4$ alkoxy, or phenyl optionally substituted with one or two halogens, $C_1$-$C_4$ alkyl groups, $C_1$-$C_4$ alkoxy groups or nitro groups, $R_8$ is $C_1$-$C_6$ alkyl or phenyl optionally substituted with one or two halogens, $C_1$-$C_4$ alkyl groups, $C_1$-$C_4$ alkoxy groups or nitro groups; $R_9$ is $C_1$-$C_6$ alkyl or phenyl optionally substituted with one or two halogens, $C_1$-$C_4$ alkyl groups, $C_1$-$C_4$ alkoxy groups or nitro groups; and the pharmaceutically and pharmacologically acceptable or a pharmaceutically and pharmacologically acceptable salt thereof; and an inert carrier.

* * * * *